(12) United States Patent
Jiang et al.

(10) Patent No.: US 8,242,318 B2
(45) Date of Patent: Aug. 14, 2012

(54) CATALYTIC HYDROGENATION

(75) Inventors: Li Jiang, Newton, MA (US); Timothy Jones, Cottenham (GB); Fenglou Zou, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 287 days.

(21) Appl. No.: 12/630,013

(22) Filed: Dec. 3, 2009

(65) Prior Publication Data

US 2010/0168454 A1    Jul. 1, 2010

(30) Foreign Application Priority Data

Dec. 29, 2008    (GB) .................. 0823557.4

(51) Int. Cl.
*C07C 5/03*    (2006.01)
*C07C 5/05*    (2006.01)
*C07C 5/02*    (2006.01)
*C07C 209/00*    (2006.01)
*C07C 51/36*    (2006.01)

(52) U.S. Cl. ........ 585/250; 585/273; 585/275; 585/277; 585/350; 585/700; 564/385; 554/141

(58) Field of Classification Search ........................ None
See application file for complete search history.

(56) References Cited

U.S. PATENT DOCUMENTS 4,851,488 A * 7/1989 Burstain .................... 526/78
6,177,567 B1 * 1/2001 Chiu et al. .................. 546/47

FOREIGN PATENT DOCUMENTS

| WO | 2005021562 A2 | 3/2005 |
| WO | 2006066863 A1 | 6/2006 |
| WO | 2008067218 A1 | 6/2008 |

OTHER PUBLICATIONS

Bell et al: "Asymmetric hydrogenation of unfunctionalized, purely alkyl-substituted olefins", Science, vol. 311, Feb. 3, 2006, pp. 642-644.
Bell et al: "Supporting online material for: Asymmetric hydrogenation of unfunctionalized, purely alkyl-substituted olefins", Science Express, Dec. 8, 2005, pp. 1-9, http://www.sciencemag.org/cgi/content/full/sci;1121977/DC1.
Brunner et al: "Hydrierung prochiraler Olefine mit Rhodium-Komplexen von optisch aktiven Amidinen", Monatshefte für Chemie, vol. 111, 1980, pp. 275-287. Abstract in English.
Catino et al: "Dirhodium(II) caprolactamate: An exceptional catalyst for allylic oxidation", Journal of the American Chemical Society, vol. 126, 2004, pp. 13622-13623.

(Continued)

*Primary Examiner* — Yate K Cutliff

(57) ABSTRACT

Catalytic hydrogenation of a double bond, notably a C=C or C=N double bond, is carried out using a homogenous catalyst which is a complex of rhodium or other transition metal containing at least one ligand which is a nitrogenous organic base. Preferably the complex is phosphorus-free and the ligand is a bicyclic base having formula

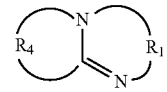

where $R_1$ and $R_4$ are hydrocarbon chains. $R_1$ preferably is a saturated chain of two carbon atoms and $R_4$ preferably is a saturated chain of three to five carbon atoms.

7 Claims, 1 Drawing Sheet

OTHER PUBLICATIONS

Chi et al: "Rhodium-catalyzed asymmetric hydrogenation", Modern Rhodium-Catalyzed Organic Reactions, edited by P. Andrew Evans, Wiley-VCH, Weinheim 2005, chapter 1, pp. 1-31.

Ezhova et al: "Characterization of a rhodiunn(III)-imine-orthometalated imine complex: reversible C-H activation of a coordinated imine", Organometallics, vol. 24, 2005, pp. 3753-3757.

Flörke et al: "Rhodium(I)-cyclooctadiene (cod) complexes with N-donor ligands 1,8-diazabicyclo[5.4.0]undec-7-ene (dbu) and 1,5-diazabicyclo[4.3.0]non-5-ene (dbn)", Acta Crystallographica, C48, 1992, pp. 1663-1665.

Flörke et al: "Rhodium(I) complexes with 1,5-diazabicyclo[4.3.0]non-5-ene (dbn) as a ligand: [RhCl(nbd)(dbn)](I) and [Rh(dbn)2(cod)][PF6](II) (nbd=norbornadiene, cod=1,5-cyclooctadiene)", Acta Crystallographica, C50, 1994, pp. 1424-1427.

Frediani et al: "Quinoline transfer hydrogenation by a rhodium bipyridine catalyst", Inorganica Chimica Acta, vol. 359, 2006, pp. 2650-2657.

Haupt et al: "Darstellung und katalytische Eigenschaften von Rhodium(I)-Komplexsalzen des Typs [Rh(COD)(o-Py(CH2)2P(Ph)(CH2)3ZR)]PF6 (Z=O, NH)", Zeitschrift für anorganische und allgemeine Chemie, vol. 619, 1993, pp. 1209-1213. Abstract in English.

Jardine: "Chlorotris(triphenylphosphine)rhodium(I): Its chemical and catalytic reactions", Progress in Inorganic Chemistry, vol. 28, 1981, pp. 63-202.

Jessop: "Homogeneous hydrogenation of carbon dioxide", Handbook of Homogeneous Hydrogenation, vol. 1, edited by Johannes G. de Vries and Cornelis J. Elsevier, Wiley-VCH, Weinheim 2007, chapter 17, pp. 489-511.

Joly et al: "Efficient enzymatic kinetic resolution of 4-hydroxytetralone and 3-hydroxyindanone", Tetrahedron: Asymmetry, vol. 12, 2001, 2283-2287.

Kaukoranta et al: "Iridium catalysts with chiral imidazole-phosphine ligands for asymmetric hydrogenation of vinyl fluorides and other olefins", Advanced Synthesis & Catalysis, vol. 350, 2008, pp. 1168-1176.

Kundu et al: "Hydroacylation of 2-vinyl benzaldehyde systems: An efficient method for the synthesis of chiral 3-substituted indanones", Journal of the American Chemical Society, vol. 127, 2005, pp. 16042-16043.

Legault et al: "Iridium catalyzed enantioselective hydrogenation of N-iminopyridinium ylides: mechanistic insights", Heterocycles, vol. 76, No. 2, 2008, pp. 1271-1283.

Menges et al: "Synthesis and application of chiral phosphino-imidazoline ligands: Ir-catalyzed enantioselective hydrogenation", Organic Letters, vol. 4, No. 26, 2002, pp. 4713-4716.

Munshi et al: "Hydrogenation of carbon dioxide catalyzed by ruthenium trimethylphosphine complexes: The accelerating effect of certain alcohols and amines", Journal of the American Chemical Society, vol. 124, 2002, pp. 7963-7971.

Oonishi et al: "Rh(I)-catalyzed hydroacylation/cycloisomerization cascade: synthesis of (±)-epiglobulol", Tetrahedron Letters, vol. 47, 2006, pp. 5617-5621.

Oro et al: "Rhodium", Handbook of Homogeneous Hydrogenation, vol. 1, edited by Johannes G. de Vries and Cornelis J. Elsevier, Wiley-VCH, Weinheim 2007, chapter 1, pp. 3-30.

Schniedermeier et al: "New rhodium(I)-π-chelate complexes with coordinated amidine bases (dbu, dbn) and their catalytic properties to polymerize phenylacetylene", Journal of Organometallic Chemistry, vol. 506, 1996, pp. 41-47.

Takeishi et al: "Rhodium-catalyzed intramolecular hydroacylation of 5- and 6-alkynals: Convenient synthesis of α-alkylidenecycloalkanones and cycloalkenones", Chemistry—A European Journal, vol. 10, 2004, pp. 5681-5688.

* cited by examiner

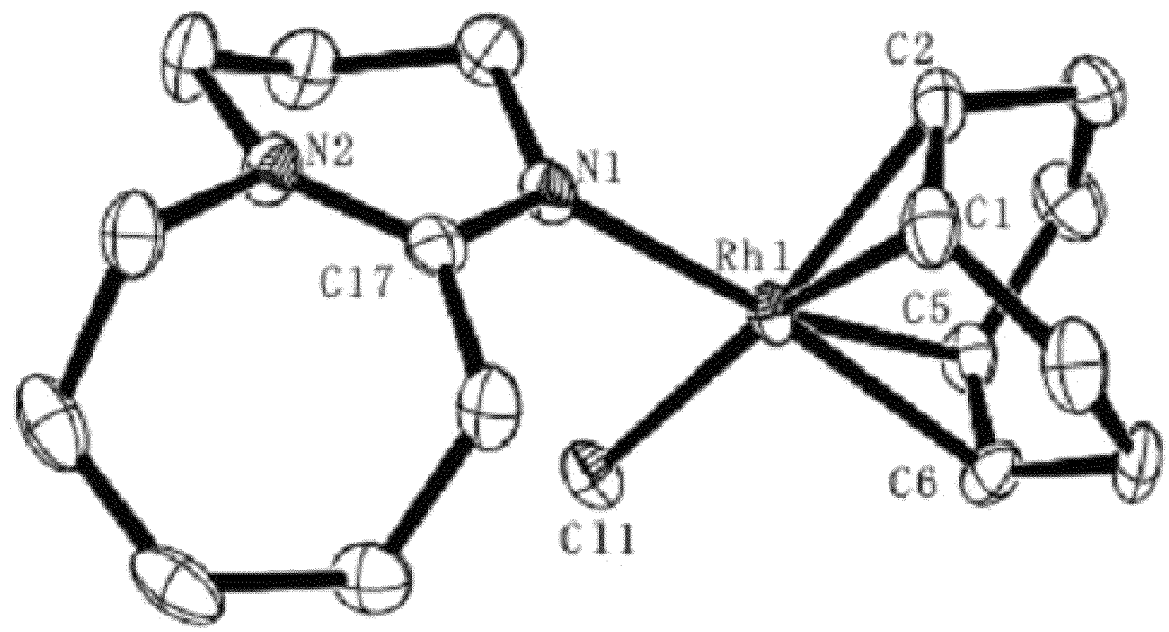

CATALYTIC HYDROGENATION

FIELD OF THE INVENTION

This invention relates to the catalytic hydrogenation of organic compounds.

BACKGROUND OF THE INVENTION

The hydrogenation of a double bond between two carbon atoms or between a carbon atom and a hetero atom is a chemical reaction which can be carried out in the presence of a catalyst. Transition metal complexes have been used as homogeneous catalysts for this reaction, but in many cases these complexes have contained phosphine ligands which tend to be expensive, unpleasant to handle and also toxic.

There have been few examples of non-phosphine ligands in catalysts for hydrogenation. Those that have been described include the following.

Frediani et al. "Quinoline transfer hydrogenation by a rhodium bipyridine catalyst", Inorganica Chimica Acta, 359, 2650-2657 (2006) have described the use of the rhodium complex cis-[Rh(bipy)2Cl2]Cl 2H2O containing the bipyridyl ligand as a catalyst for hydrogenation.

Brunner and Agrifoglio "Hydrogenation of prochiral olefins with rhodium complexes of optically active amidines", Monatshefte für Chemie, 111, 275-287 (1980) have disclosed olefin hydrogenation using a rhodium compound in the presence of an amidine compound. They used amidines having a general formula:

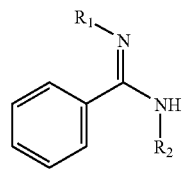

in which R1 was 1-methylbenzyl and R2 was benzyl, phenyl, isopropyl or 1-methylbenzyl.

SUMMARY OF THE INVENTION

The present invention provides a process for hydrogenating a compound at a double bond between carbon and another atom—by contacting the compound with hydrogen in the presence of a catalytic complex, characterized in that the complex is a transition metal complex containing a ligand which is a heterocyclic organic base of the formula

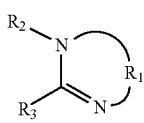

wherein $R_1$ comprises a substituted or unsubstituted hydrocarbon chain of at least two carbon atoms and $R_2$ and $R_3$ are substituted or unsubstituted hydrocarbon groups or $R_2$ and $R_3$ together are a substituted or unsubstituted hydrocarbon chain of at least two carbon atoms. It is preferred that $R_2$ and $R_3$ provide saturated aliphatic hydrocarbon chains but they may be substituted and the substituent groups may be aliphatic or aromatic.

When the ligand is a bicyclic aliphatic compound in which $R_2$ and $R_3$ together form a single hydrocarbon chain, the ligand can be represented by the formula

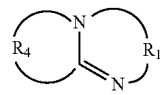

where $R_1$ is as defined above and $R_4$ represents the hydrocarbon chain of at least two carbon atoms provided by $R_2$ and $R_3$ together.

$R_1$ may be a chain of 2 up to 5 or possibly up to 8 carbon atoms especially 2 or 3 carbon atoms. $R_4$ may be an aliphatic hydrocarbon chain of 2 up to 6 or possibly up to 10 carbon atoms, especially of 3 to 5 carbon atoms. $R_1$ and $R_4$ may both be saturated aliphatic groups, optionally bearing side-chain groups which may be aliphatic, notably $C_1$ to $C_4$ alkyl, or may be aromatic.

The catalyst may contain at least one other ligand. A second ligand may be a cycloaliphatic diene, notably 1,5-cyclo-octadiene. Preferably the catalyst does not contain phosphorus.

A catalytic complex used in this invention may contain one or two metal atoms, generally with at least two ligands per metal atom. The transition metal in the complex is preferably from groups VB, VIIB, VIIB, or VIIIB of the periodic table. It may be a transition metal with atomic number in the ranges from 41 to 45 and 73 to 77. The metal may be rhodium, which has atomic number 45. It is particularly envisaged that the molecule may contain one rhodium atom with one ligand of the formula

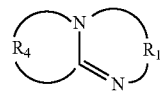

discussed above and one other ligand which may be a cycloaliphatic diene, notably 1,5-cyclo-octadiene.

The catalyst maybe Rh(DBU)(COD)Cl or Rh(DBN)(COD)Cl where DBU denotes 1,8-diazabicyclo[5.4.0]undec-7-ene which has the formula

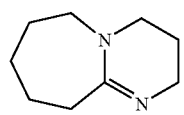

DBN denotes 1,5-diazabicyclo[4.3.0]non-5-ene which has the formula

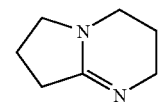

and COD denotes 1,5 cyclo-octadiene which has the formula

DBN and DBU are strong uncharged nitrogenous bases but are bulky, sterically hindered molecules and consequently are weak nucleophiles.

The hydrogenation reaction will generally be carried out using hydrogen gas with the substrate molecule and the catalyst in solution in an organic solvent. The reaction temperature may possibly range from 0 to 80° C. although temperatures outside this range are also possible.

BRIEF DESCRIPTION OF THE DRAWING

The sole drawing FIGURE illustrates the structure of the complex Rh(DBU)(COD)Cl as determined by X ray crystallography.

DETAILED DESCRIPTION

In these examples, all operations with air-sensitive complexes were performed under an inert atmosphere of dry $N_2$ using standard Schlenk techniques or in a glove box (MBRAUN Labmaster SP). All solvents (including deuterated solvents) were dried and deoxygenated using sodium/benzophenone, and then distilled under nitrogen. IR spectra were obtained using a Nicolet 800 FT-IR spectrometer and NMR spectra were recorded on a Bruker AVANCE 400 spectrometer ($^1H$ at 400.1 MHz and $^{13}C$ at 100.6 MHz) and spectra are reported relative to tetramethylsilane.

Preparative Example

Preparation and Characterisation of Rh(DBU)(COD)Cl 38.1644 mg [Rh(COD)Cl]$_2$ (0.0774 mmol) was dissolved in ca. 5 ml toluene, and 0.3719 mmol DBU (56.6181 mg) was then added. The reaction mixture was stirred at 70° C. for 16 hours. The reaction mixture was dried in vacuum, and then washed with hexane. The remaining solid was dried again, and then dissolved in benzene. By carefully layering the benzene solution with hexane, yellow crystals were obtained which were used for single crystal X-ray diffraction study. The yield of Rh(DBU)(COD)Cl was 50.8612 mg (0.1275 mmol, 82.36%).

The results for $^{13}C$ {H} NMR spectroscopy were (100.6 MHz, benzene-d$_6$, 298K):

| | |
|---|---|
| δ 82.91 ppm (d, 1C, J ($^{103}$Rh, $^{13}$C) = 12 Hz), | Four carbon atoms |
| δ 81.83 ppm (d, 1C, J ($^{103}$Rh, $^{13}$C) = 12 Hz), | of COD, coordinated to |
| δ 73.42 ppm (d, 1C, J ($^{103}$Rh, $^{13}$C) = 14 Hz), | rhodium |
| δ 73.22 ppm (d, 1C, J ($^{103}$Rh, $^{13}$C) = 15 Hz), | |
| δ 32.24 ppm (s, 1C), δ 31.68 ppm (s, 1C), | Four carbon atoms of |
| δ 31.04 ppm (s, 1C), δ 30.71 ppm (s, 1C), | COD |
| δ 163.36 ppm (s, 1C), δ 52.84 ppm (s, 1C), | Nine carbon atoms of |
| δ 47.21 ppm (s, 1C), δ 41.17 ppm (s, 1C), | DBU |
| δ 39.33 ppm (s, 1C), δ 29.37 ppm (s, 1C), | |
| δ 27.70 ppm (s, 1C), δ 25.35 ppm (s, 1C), | |
| δ 22.34 ppm (s, 1C). | |

In this $^{13}C$ {H} NMR spectrum the carbon of C=N of bound DBU shows a singlet at δ 163.36 ppm; the carbon nuclei of bound C=C trans to N show two doublets at δ 82.91 ppm and δ 81.83 ppm, respectively, with J(Rh, C) of 12 Hz each, while the carbon nuclei of bound C=C trans to Cl show two doublets at δ 73.42 ppm (J(Rh, C)=14 Hz) and δ 73.22 ppm (J(Rh, C)=15 Hz), respectively.

The corresponding results for $^1H$ NMR spectroscopy were (400.1 MHz, benzene-d$_6$, 298K):

| | |
|---|---|
| δ 7.27 ppm (s) | solvent, benzene-d$_6$ |
| δ 5.10 ppm (bs, 1H,) δ 5.02 ppm (bs, 1H,), | Four protons at double |
| δ 3.70 ppm (bs, 1H,) δ 3.64 ppm (bs, 1H,), | bonds of COD |
| δ 3.78 ppm (m, 1H) δ 3.09 ppm (m, 1H) | DBU protons |
| δ 3.56 ppm (m, 1H) δ 3.24 ppm (m, 1H) | |
| δ 2.48 ppm (m, 8H) | Four protons of DBU and four protons of COD |
| δ 2.07 ppm (m, 1H) | DBU proton |
| δ 1.76 ppm (m, 4H) | Four protons of COD |
| δ 1.64 ppm (m, 1H) δ 1.60 ppm (m, 1H) | DBU protons |
| δ 1.28 ppm (bs, 1H) δ 1.40 ppm (bs, 1H) | |
| δ 1.30 ppm (bs, 1H) δ 1.07 ppm (bs, 2H) | |

In this $^1H$ NMR spectrum the HC=CH trans to N shows two broad singlets at δ 5.10 ppm and δ 5.02 ppm compared with the HC=CH trans to Cl showing two broad singlets at δ 3.70 and δ 3.64 ppm.

The observed elemental analysis (expressed in weight percent) was: C, 51.30; H, 7.05, N, 6.98, Cl: 8.34, which is in good agreement with the calculated elemental percentages: C, 51.20; H, 7.08; N, 7.02; Cl, 8.89.

The drawing shows the X-ray crystal structure of the complex Rh(DBU)(COD)Cl with hydrogen atoms omitted. The DBU is coordinated with a Rh center via an imino-nitrogen located trans to a C=C in COD. The complex adopts a slight distorted square planar geometry around the Rh center, which is similar to the complex Rh(PPh$_3$)$_3$Cl (Ph=phenyl) that is known as Wilkinson's catalyst. The bond lengths of Rh(1)-C (6) and Rh(1)-C(5) trans to the nitrogen atom are longer than those of Rh(1)-C(2) and Rh(1)-C(1), which are trans to the chlorine atom.

Rh(DBU)(COD)Cl crystals were still stable after being exposed to air for 4 days, indicating low sensitivity to oxygen and moisture.

Examples of Catalytic Hydrogenation of C=C and C=N Double Bonds

The catalytic activity of Rh(DBU)(COD)Cl to the hydrogenation of various C=C, C=N and C=O bonds was evaluated. Table 1 shows the compounds hydrogenated using the catalyst Rh(DBU)(COD)Cl, the hydrogenation products, the conversion (or yield) of the reaction and the turnover number (TON) of the catalytic cycle. Turnover number is the average number of substrate molecules hydrogenated per catalyst molecule The details of the reactions are described in the following examples.

Example 1

Hydrogenation of N-Benzylidenebenzylamine to Dibenzylamine

Working in a glove box, a mixture of Rh(DBU)(COD)Cl (6.30 mg, 0.0158 mmol), N-benzylidenebenzylamine (403.19 mg, 2.065 mmol) and approximately 2 ml dimethyl sulphoxide (DMSO) was prepared in a 20 ml glass vessel with a gas admission valve. The reaction mixture was pressured with 1.5 bar hydrogen gas and stirred for 16 hours at a temperature of 50° C., after which time the solution turned from its original colour of bright yellow to a dark brown. Integration of peaks in the $^1H$ NMR spectrum of the reaction mixture revealed a conversion rate of 13.4% and a TON of 18.

Example 2

Hydrogenation of N-Benzylideneaniline to N-Benzylaniline

A mixture of Rh(DBU)(COD)Cl (4.46 mg, 0.0112 mmol), N-benzylideneaniline (246.4 mg, 1.360 mmol) and approximately 2 ml DMSO was prepared in a 20 ml glass vessel with a gas admission valve, located in a glove box. The reaction mixture was pressured with 1.5 bar hydrogen gas and stirred for 16 hours at a temperature of 50° C., after which time the solution turned from its original colour of bright yellow to a dark brown. Integration of peaks in the $^1$H NMR spectrum of the reaction mixture showed a conversion rate of 91.6% and a TON of 111.

Example 3

Hydrogenation of Cyclohexene to Cyclohexane

A mixture of Rh(DBU)(COD)Cl (5.14 mg, 0.0129 mmol), cyclohexene (1.14065 g, 13.887 mmol) and sufficient toluene to dissolve the catalyst was prepared in a 20 ml glass vessel with a gas admission valve, located in a glove box. The reaction mixture was pressured with 1.5 bar hydrogen gas and stirred for 16 hours at a temperature of 50° C. Integration of peaks in the $^1$H NMR spectrum of a small sample of the reaction mixture dissolved in deuterated chloroform (CDCl$_3$) showed a conversion rate of 20.6% and a TON of 222.

Example 4

Hydrogenation of 2,3-Dimethyl-2-Butene to 2,3-Dimethyl-2-Butane

A mixture of Rh(DBU)(COD)Cl (5.97 mg, 0.0150 mmol), 2,3-dimethyl-2-butene (0.93469 g, 11.106 mmol) and sufficient toluene to dissolve the catalyst was prepared in a 20 ml glass vessel with a gas admission valve, located in a glove box. The reaction mixture was pressured with 1.5 bar hydrogen gas and stirred for 16 hours at a temperature of 50° C. Integration of peaks in the $^1$H NMR spectrum of a small sample of the reaction mixture dissolved in CDCl$_3$ showed indicated a conversion rate of 7.8% and a TON of 58.

Example 5

Hydrogenation of 1,4-Cyclohexadiene to Cyclohexene and Cyclohexane

A mixture of Rh(DBU)(COD)Cl (4.79 mg, 0.0120 mmol), 1,4-cyclohexadiene (0.92612 g, 11.558 mmol) and sufficient toluene to dissolve the catalyst was prepared in a 20 ml glass vessel with a gas admission valve, located in a glove box. The reaction mixture was pressured with 1.5 bar hydrogen gas and stirred for 16 hours at a temperature of 50° C. Integration of peaks in the $^1$H NMR spectrum of a small sample of the reaction mixture dissolved in CDCl$_3$ showed a conversion rate of 16.1% for cyclohexene and 5.1% for cyclohexane, which corresponded to a TON of 155 for cyclohexene and a TON of 49 for cyclohexane, respectively.

Example 6

Hydrogenation of Oleic Acid to Stearic Acid

A mixture of Rh(DBU)(COD)Cl (4.02 mg, 0.0101 mmol), oleic acid (1.04317 g, 3.693 mmol) and approximately 0.3 ml of deuterated benzene (C$_6$D$_6$) was prepared in a 20 ml glass vessel with a gas admission valve, located in a glove box. The reaction mixture was pressured with 1.5 bar hydrogen gas and stirred for 14 hours at a temperature of 50° C. All of the liquid had disappeared during the course of the reaction and only a white solid was observed. A small sample of the white solid was dissolved in benzene-d$_6$. Integration of peaks in the $^1$H NMR spectrum of this solution indicated a conversion rate of 89.0% and a TON of 329.

TABLE 1

Hydrogenation of compounds with C=C and C=N bonds

| Example | Substrate | product | Conversion | Substrate/Cat. | TON |
|---|---|---|---|---|---|
| 1 | Ph-CH$_2$-N=CH-Ph | Ph-CH$_2$-NH-CH$_2$-Ph | 13.4% | 130.8 | 18 |
| 2 | Ph-N=CH-Ph | Ph-NH-CH$_2$-Ph | 91.6% | 121.6 | 111 |
| 3 | cyclohexene | cyclohexane | 20.6% | 1077.6 | 222 |
| 4 | 2,3-dimethyl-2-butene | 2,3-dimethylbutane | 7.8% | 742.6 | 58 |
| 5 | 1,4-cyclohexadiene | cyclohexene/cyclohexane | 16.1%/5.1% | 963.3 | 155/49 |
| 6 | C$_8$H$_{17}$CH=CHC$_7$H$_{14}$COOH | C$_8$H$_{17}$CH$_2$—CHC$_7$H$_{14}$COOH | 89.0% | 369.3 | 329 |

The invention claimed is:

1. A process for hydrogenating a compound at a double bond between carbon and another atom by contacting the compound with hydrogen in the presence of a catalytic complex, characterized in that the complex is a rhodium complex containing a ligand which is a heterocyclic organic base of the formula

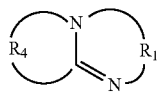

where $R_1$ comprises a substituted or unsubstituted saturated hydrocarbon chain of 2 to 8 carbon atoms and $R_4$ is a substituted or unsubstituted saturated hydrocarbon chain of 2 to 10 carbon atoms,
the complex further containing a second organic ligand which is a cycloaliphatic diene.

2. The process of claim 1 wherein $R_1$ is a substituted or unsubstituted saturated hydrocarbon chain of 2 to 5 carbon atoms and $R_4$ is a substituted or unsubstituted saturated hydrocarbon chain of 2 to 6 carbon atoms.

3. The process of claim 1 wherein $R_1$ is a substituted or unsubstituted saturated hydrocarbon chain of 2 or 3 carbon atoms and $R_4$ is a substituted or unsubstituted saturated hydrocarbon chain of 3 to 5 carbon atoms.

4. The process of claim 1 wherein the cycloaliphatic diene is a 1,5-cyclo-octadiene.

5. The process of claim 1 wherein hydrogenation takes place at a carbon-carbon double bond.

6. The process of claim 1 wherein hydrogenation takes place at a carbon-nitrogen double bond.

7. A process according to claim 4 wherein $R_1$ is a substituted or unsubstituted saturated hydrocarbon chain of 3 carbon atoms and $R_4$ is a substituted or unsubstituted saturated hydrocarbon chain of 3 to 5 carbon atoms.

* * * * *